(12) United States Patent
Robertson

(10) Patent No.: US 7,436,596 B2
(45) Date of Patent: Oct. 14, 2008

(54) OPTICAL SENSOR BASED ON SURFACE ELECTROMAGNETIC WAVE RESONANCE IN PHOTONIC BAND GAP MATERIALS AND METHOD FOR USING SAME

(76) Inventor: William M. Robertson, 1310 Roberts Rd., Goodlettsville, TN (US) 37072

( * ) Notice: Subject to any disclaimer, the term of this patent is extended or adjusted under 35 U.S.C. 154(b) by 13 days.

(21) Appl. No.: 11/468,343

(22) Filed: Aug. 30, 2006

(65) Prior Publication Data

US 2007/0047088 A1 Mar. 1, 2007

Related U.S. Application Data

(60) Provisional application No. 60/712,682, filed on Aug. 30, 2005, provisional application No. 60/806,210, filed on Jun. 29, 2006.

(51) Int. Cl.
*G02B 1/10* (2006.01)
(52) U.S. Cl. .................. 359/587; 359/588; 359/589
(58) Field of Classification Search ............... 359/587, 359/588, 589
See application file for complete search history.

(56) References Cited

U.S. PATENT DOCUMENTS

| | | | |
|---|---|---|---|
| 3,996,461 A * | 12/1976 | Sulzbach et al. | 250/214 R |
| 4,844,613 A | 7/1989 | Batchelder et al. | |
| 4,997,278 A | 3/1991 | Finlan et al. | |
| 6,594,011 B1 | 7/2003 | Kempen | |
| 6,665,119 B1 * | 12/2003 | Kurtz et al. | 359/486 |
| 6,801,317 B2 | 10/2004 | Hofmann | |
| 2004/0130723 A1 * | 7/2004 | Yager et al. | 356/445 |
| 2004/0258348 A1 * | 12/2004 | Deliwala | 385/14 |
| 2007/0008546 A1 * | 1/2007 | Ho et al. | 356/481 |

OTHER PUBLICATIONS

Villa et al., "Photonic crystal sensor based on surface waves for thin-film characterization," Optics Letters, Apr. 15, 2002, pp. 646-648, vol. 27, No. 8, Optical Society of America, US.

Otsuki et al., "Wavelength-scanning surface plasmon resonance imaging," Applied Optics, Jun. 10, 2005, pp. 3468-3472, vol. 44, No. 17, Optical Society of America, US.

Liedberg et al., "Surface Plasmon Resonance for Gas Detection and Biosensing," Sensors and Actuators, May 31, 1983, pp. 299-304, vol. 4, Elsevier Sequoia, The Netherlands.

(Continued)

*Primary Examiner*—Joshua L Pritchett
(74) *Attorney, Agent, or Firm*—Wayne Edward Ramage; Baker Donelson

(57) ABSTRACT

A sensing method and apparatus using photonic band gap multilayered material. Photonic band gap multi-layers are formed from alternating layers of higher refractive index and lower refractive index materials, and may be deposited or disposed on a optically transparent substrate or a reflecting face of a prism. Light is directed into the prism, directed to the photonic band gap multilayer, and reflected out of the prism, where it is captured and analyzed. Various sensor configurations keep light wavelength or coupling angle fixed, while monitoring the change in the other parameter. Also disclosed is a microarray configuration with an array of probe spots placed on one surface of the multilayer, which is mounted on an x-y translation stage.

7 Claims, 10 Drawing Sheets

OTHER PUBLICATIONS

Shinn et al., "Surface plasmon-like sensor based on surface electromagnetic waves in photonic band-gap material," Sensors and Actuators B, Aug. 7, 2004, pp. 360-364, vol. 105, Elsevier B.V., U.S.

Robertson, "Experimental Measurement of the Effect of Termination on Surface Electromagnetic Waves in One-Dimensional Photonic Bandgap Arrays," Journal of Lightwave Technology, Nov. 1999, pp. 2013-2017, vol. 17, No. 11, IEEE, US.

Robertson et al., "Surface electromagnetic wave excitation on one-dimensional photonic band-gap arrays," Applied Physics Letters, Mar. 29, 1999, pp. 1800-1802, vol. 74, No. 13, American Institute of Physics, US.

Liedberg et al., "Principles of biosensing with an extended coupling matrix and surface plasmon resonance," Sensors and Actuators B, 1993, pp. 63-72, vol. 11, Elsevier Sequoia, US.

International Preliminary Report on Patentability and Written Opinion of the International Searching Authority, PCT/US2006/033891.

* cited by examiner

OPTICAL SENSOR BASED ON SURFACE ELECTROMAGNETIC WAVE RESONANCE IN PHOTONIC BAND GAP MATERIALS AND METHOD FOR USING SAME

This application claims priority to Provisional Patent Application No. 60/712,682, filed Aug. 30, 2005, by William M. Robertson, and Provisional Patent Application No. 60/806,210, filed Jun. 29, 2006, by William M. Robertson, and is entitled in whole or in part to those filing dates for priority. The specification, drawings, and attachments of Provisional Patent Application Nos. 60/712,682 and 60/806,210 are incorporated herein in their entirety by reference.

FIELD OF INVENTION

The invention disclosed herein involves optical sensing configurations designed to detect trace amounts of biological and chemical entities, as well as methods for utilizing these sensors. In particular, one embodiment of the present invention is directed towards a sensor and method of microarray analysis using surface optical wave resonance in photonic band gap films.

BACKGROUND

Surface plasmon sensors are a class of sensors with a long and commercially successful history. They are principally used to detect small amounts of biological entities. The active element of a surface plasmon sensor is a metal film. In a typical surface plasmon sensor the metal surface is prepared with an antibody to a particular protein bound to the metal surface. The angle of surface plasmon coupling is determined and then the film is exposed (usually by the use of a flow cell) to a sample that is being tested for the targeted protein. If the protein is present in the sample solution it binds to the antibody adding a dielectric-loading layer to the metal surface. This extra layer leads to an alteration in the angle of surface plasmon coupling, thus indicating the presence of the protein. The metal film thickness is typically about one tenth of the wavelength of the incident light. At angles of incidence, $\theta$, greater than the angle for total-internal reflection the light creates an evanescent field that can penetrate through the metal. Surface plasmons are resonantly generated at the angle of incidence at which the wave vector and frequency of the evanescent field match those of surface plasmons at the metal-air interface. The most obvious manifestation of this coupling is a drop in the intensity of the reflected light.

In practice, surface plasmon sensors have some limitations. Because of its sharp resonance, silver would appear to be the best material for making sensors with high surface sensitivity. However, because silver is chemically reactive it is not suitable in most applications. Similar reactivity issues eliminate copper and aluminum. Gold is thus the standard material for essentially all commercially available surface plasmon sensors. However, gold has a less well-defined resonance than silver because of its higher dielectric loss. Gold films have limited sensitivity to dielectric changes at the surface because of the difficulty of accurately detecting small angle shifts of the broad resonance. Furthermore, the optical properties of gold mean that it only supports surface plasmons at longer wavelengths in the red and infrared.

Microarray-based assay methods also have become a mainstay of biological research, particularly in the areas of genomics and proteomics. Existing microarray readout technologies, however, have several limitations. For example, current microarray methods use fluorescent, colorimetric, or radioactive tags or labels to detect binding. Fluorescent labels currently are the most common detection strategy, but suffer from problems of low sensitivity, high background interference, and cross-reactivity. These problems are exacerbated in the case of proteins where the presence of a fluorophore can alter a protein's binding properties.

Accordingly, what is needed is an optical sensor apparatus that circumvents the limitations imposed by chemical reactivity, dielectric loss, and wavelength operating range. Further, a microarray-based sensor apparatus is needed that avoids the problems of low sensitivity, high background interference, and cross-reactivity associated with existing microarray technologies.

SUMMARY OF THE INVENTION

The present invention provides for an optical multilayer structure constructed so as to cause the structure to exhibit a photonic band gap. In one exemplary embodiment, the structure comprises an optical multilayer deposited or disposed on an optically transparent substrate or side of a prism, the optical multilayer being formed of a series of alternative layers of high refractive index materials and low refractive index materials. The thickness of the layers is selected so as to cause the structure to exhibit a photonic band gap. A terminating layer deposited on the multilayer such that a surface optical mode exists at a wavelength within the photonic band gap. A sensing layer may be deposited on the terminating layer.

In an exemplary embodiment, an optical multilayer structure attached or deposited on a prism is deployed in an optical sensing apparatus suitable for testing. Light emitted from a light source passes into prism, interacts with the optical multilayer structure, and is reflected out through the prism, where it can be captured and analyzed. Capturing devices may include, but are not limited to, optical spectrometers, a screen, a CCD camera, or a CCD array.

In one embodiment of the optical sensing apparatus, the light source provides light with a band of wavelengths, and the light is collimated by a lens or otherwise before passing into the prism. The angle of incidence of the light on the optical multilayer structure is constant, and above the angle for total internal reflection.

In another embodiment of the optical sensing apparatus, the light source has a fixed stable wavelength (e.g., a laser), and the light is focused by a lens or otherwise before passing into the prism. A focal point thus is created on the optical multilayer structure. The focal point can be moved to various points on the optical multilayer structure.

In yet another embodiment, an array of probe spots are placed on the surface of the optical multilayer structure. A reference scan is performed using collimated light from the light source, which is focused on the optical multilayer structure. The multilayer structure is moved so that the focal point covers the entire array. The array is exposed to the target or targets of the test, and a second scan is performed. Comparison of the reference scan and the second scan can determine where binding has occurred.

DETAILED DESCRIPTION OF EXEMPLARY EMBODIMENTS

Figure 1:
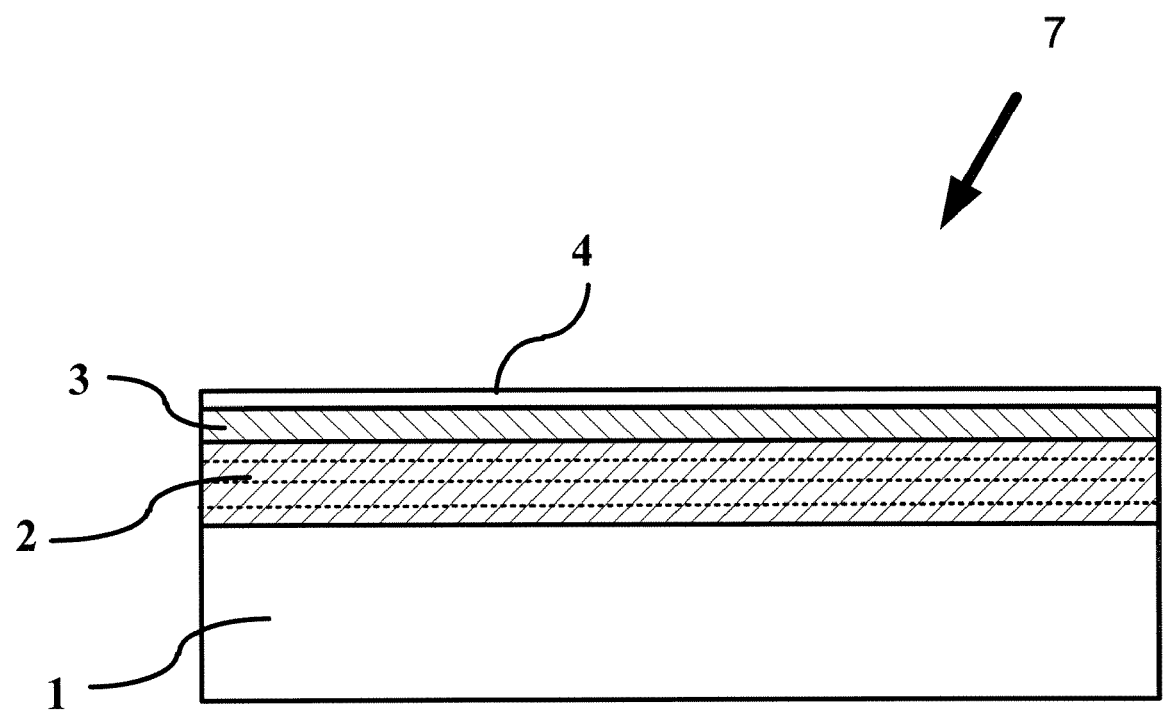
FIG. 1 is a side view of a multilayer structure in accordance with one embodiment of the present invention.

Surface electromagnetic (EM) waves are electromagnetic modes that propagate at the interface between a passive dielectric material and a so-called active medium (i.e., one whose real part of the dielectric function is less than −1 at the frequency of interest). The dispersion of surface EM waves is such that they are non-radiative, which means that they do not couple directly to light. Excitation of surface EM modes requires the use of a prism or a grating configuration in order to phase match incident light to the surface mode and facilitate resonant coupling between light and the surface EM modes.

The most widely studied type of surface electromagnetic waves are those that exist at the surfaces of metals. These modes are known as surface plasmons. A number of metals exhibit a sufficiently negative real part of the dielectric function so as to support surface plasmons; however, most metals also have strong dielectric loss (i.e., the large imaginary part of the dielectric function), which means that the resonant excitation of surface plasmons is heavily damped. In practice, there are a handful of metals with low loss that exhibit pronounced surface plasmon effects—e.g., silver, gold, copper, and aluminum. Silver and aluminum are the best across wavelengths in the visible range. Gold and copper show good surface plasmon effects in the red and infrared range.

Photonic band gap (PBG) materials are periodic composites that can be engineered to exhibit metal-like optical properties over given frequency intervals. A PBG material is composed of two constituents with different dielectric constants arranged with a regular periodicity in one, two, or three dimensions. The coherent effects of scattering and interference result in a dramatic modification of the dispersion relation for light traveling in the composite, including the appearance of photonic band gaps—frequency intervals in which the propagation of light is forbidden. In the forbidden transmission regions, the PBG material has metal-like behavior and the optical response of the composite can be described by an effective dielectric constant with a negative real value. It is this negative effective dielectric constant that permits the material to support surface EM waves at frequencies within the forbidden transmission band.

The existence of surface EM waves in PBG materials is well known both theoretically and experimentally. One of the earliest experimental demonstrations of prism coupling to surface EM waves was in a two-dimensional periodic PBG array at microwave frequencies. To date, most photonic band gap experiments with two- or three-dimensionally periodic systems are performed at long wavelengths (microwave to infrared) because of the difficulty of fabricating structures with periodicities on an optical length scale. Although the situation is changing as nano-fabrication techniques become more sophisticated, two- and three-dimensional PBG materials for visible wavelength are still in the realm of the research lab. One advantage of the one-dimensional periodic systems is that they can be accurately fabricated using well-developed commercial thin film deposition technology. Software simulation tools may be used to accurately predict the surface EM wave response of a given multilayer structure.

Surface EM waves in PBG materials have some distinct differences from surface plasmons. For sensing applications there are two differences that are particularly important. First, the dielectric loss in PBG materials is determined by the loss of the constituent materials and it is typically orders of magnitude lower than the dielectric loss of even the best surface plasmon active metals. Low dielectric loss translates into very sharp surface EM wave resonance excitation and concomitantly enhanced sensitivity. Although the question of sensor performance is complex, in simple terms PBG-based sensors can be orders of magnitude more sensitive than surface plasmon sensors. Second, the response of the one-dimensional PBG material can be engineered so that surface waves can be generated at any wavelength. In contrast, for surface plasmon phenomena the dielectric properties of the metal determine the wavelength range of operation. For example, gold, the most commonly used surface plasmon sensing material, is limited to wavelengths in the red and infrared.

FIG. 1 shows a schematic representation of an optical multilayer structure 7 that supports the generation of surface EM waves and is suitable for sensing applications, in accordance with one exemplary embodiment of the present invention. The optical multilayer structure 7 comprises a multilayer 2 deposited or otherwise disposed on a substrate 1. The substrate 1 typically is optically transparent and may be made of any suitable material, such as, but not limited to, glass. In one exemplary embodiment the substrate 1 may be a glass microscope slide.

In an exemplary embodiment, the multilayer 2 consists of alternating layers of high refractive index and low refractive index materials. There may be as few as one high refractive index material layer and one low refractive index material layer. Where there are multiple layers of each, the high refractive index material layers may contain the same or different materials, and the same may be true for the low refractive index material layers. In one exemplary embodiment, the high refractive index material is $TiO_2$ and the low refractive index material is $SiO_2$, although other suitable materials may be used. Examples of other low refractive index materials include, but are not limited to, magnesium fluoride ($MgF_2$) and cryolite ($Na_3AlF_6$). Examples of other high index materials include, but are not limited to, silicon nitride, zinc sulphide (ZnS) and cerium oxide ($CeO_2$).

The layers in the multilayer 2 can be deposited using one of a variety of techniques that are used to create optical filters and mirrors—examples of these techniques include, but are not limited to, sputter coating and chemical vapor deposition. The layer thickness values are selected such that the structure 7 exhibits a photonic band gap (i.e., a frequency interval over which optical transmission is strongly attenuated due to the effects of destructive interference in the multilayer) at the operation wavelength and/or angle of incidence of the sensor apparatus in which the structure 7 is to be sued. Although there are other layer parameters that can result in a photonic band gap, in an exemplary embodiment the most straightforward is to select thickness values, $d_i$, for the $i^{th}$ layer based on the relation $$d_i = \frac{\lambda}{4n_i \cos\theta_i}$$

where $\lambda$ is the wavelength of operation of the sensor, and $n_i$ and $\theta_i$ are respectively the refractive index and the angle of propagation of the light in the $i^{th}$ layer.

The structure 7 may have a terminating layer 3 deposited or disposed upon the multilayer 3. As shown in FIG. 1, the terminating layer 3 may be deposited or disposed on the multilayer 3 opposite the substrate 1. The terminating layer 3 may used to adjust the position of the surface electromagnetic waves mode within the PBG. The terminating layer 3, which can be either a high or low refractive index layer, does not necessarily have the same thickness as the other layers of the same or similar type, if any, in the multilayer 2. Adjusting the terminating layer 3 thickness may set the location of the surface electromagnetic wave mode within the PBG. The thickness required to set the surface electromagnetic wave mode at any position within the PBG depends on the parameters of the multilayer 2 (e.g., refractive indices and number of bilayers). The optical response of the multilayer 2 may be accurately calculated using Fresnel's equations. Locating the mode close to the center of the PBG leads to a surface electromagnetic wave mode that is strongly confined to the surface.

As shown in FIG. 1, the structure 7 may have a sensing layer 4, which may deposited or disposed on the terminating layer 3. In one exemplary embodiment, the sensing layer 4 is designed to react with a specific entity, leading either to a mass loading and/or to an index change in the sensing layer 4. This change in surface conditions results in a change in the optical coupling to the surface electromagnetic waves in the underlying multilayer 2. Detecting a change in coupling conditions due to a surface reaction in the sensing layer 4 is the basis of sensor action.

The form of the sensing layer 4 can have many variations, depending on the nature of the sensor. In a simple gas sensor, for example, the sensing layer 4 consists of a thin layer that reacts when exposed to a specific chemical species to create a layer with altered optical characteristics (for example, Teflon AF 1600 reacts with organic vapors such as methyl ethyl ketone or acetone). For the detection of biological entities such as proteins (e.g., antibody-antigen) or DNA (e.g., DNA-DNA or DNA-probe), the sensing layer 4 may consist of an attachment layer onto which a probe for a specific species can be anchored. Examples of attachment layers include, but are not limited to, amine-terminated groups in the case of proteins, or aldehyde-terminated groups in the case of DNA. Examples of probe species and their targets include, but are not limited to, Bovine Serum Albumen (BSA)-anti-BSA and DNA probe-DNA for influenza.

Many types and examples of sensing layers have been developed for surface plasmon sensors. Some of these systems are designed specifically for the metal substrates (usually gold) used in surface plasmon sensing. However, most of these sensing layers can be adapted for use with the present invention.

In yet another exemplary embodiment, no sensing layer is present. This may be used, for example, to detect the change in refractive index of a fluid, and the multilayer structure is exposed to the fluid. In an application in which a fluid abuts the multilayer, sensing can result from changes in the refractive index of the fluid itself; as, for example, when pure water is replaced by a sugar solution in a flow cell. The arrangement can be used with both fixed wavelength and fixed angle configurations, among others.

The optical multilayer structure 7 can be used in several different sensor configurations. Some of these configurations may be similar to those used for surface plasmon sensors. In many cases, however, the very narrow surface electromagnetic wave resonance in the case of optical multilayers places more stringent requirements on the optical configurations such that a direct substitution of a multilayer in an existing configuration designed for surface plasmon operation is not possible.

Figure 2:
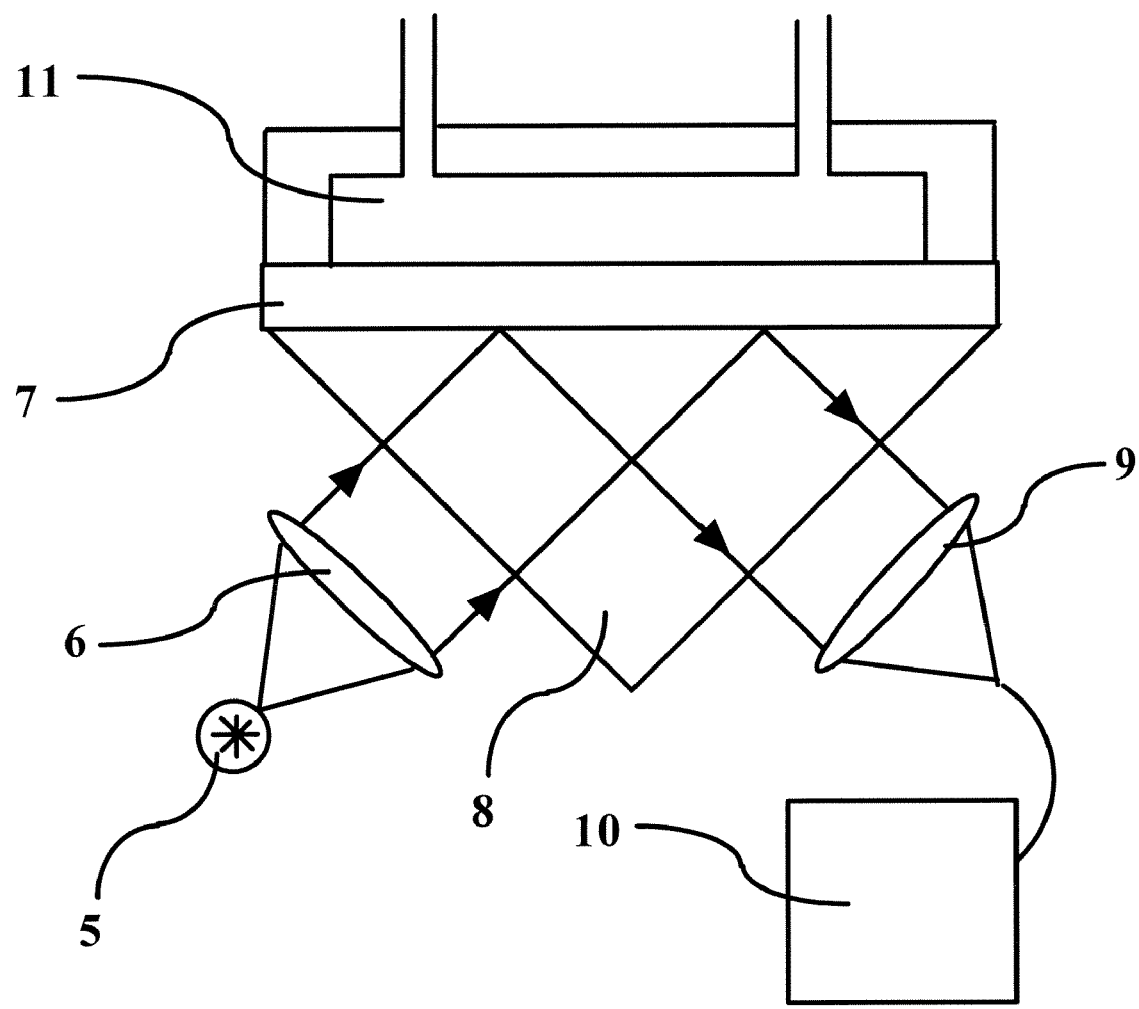
FIG. 2 is a top view of a schematic layout of the elements of an optical coupling arrangement in accordance with one embodiment of the present invention.
Figure 5:
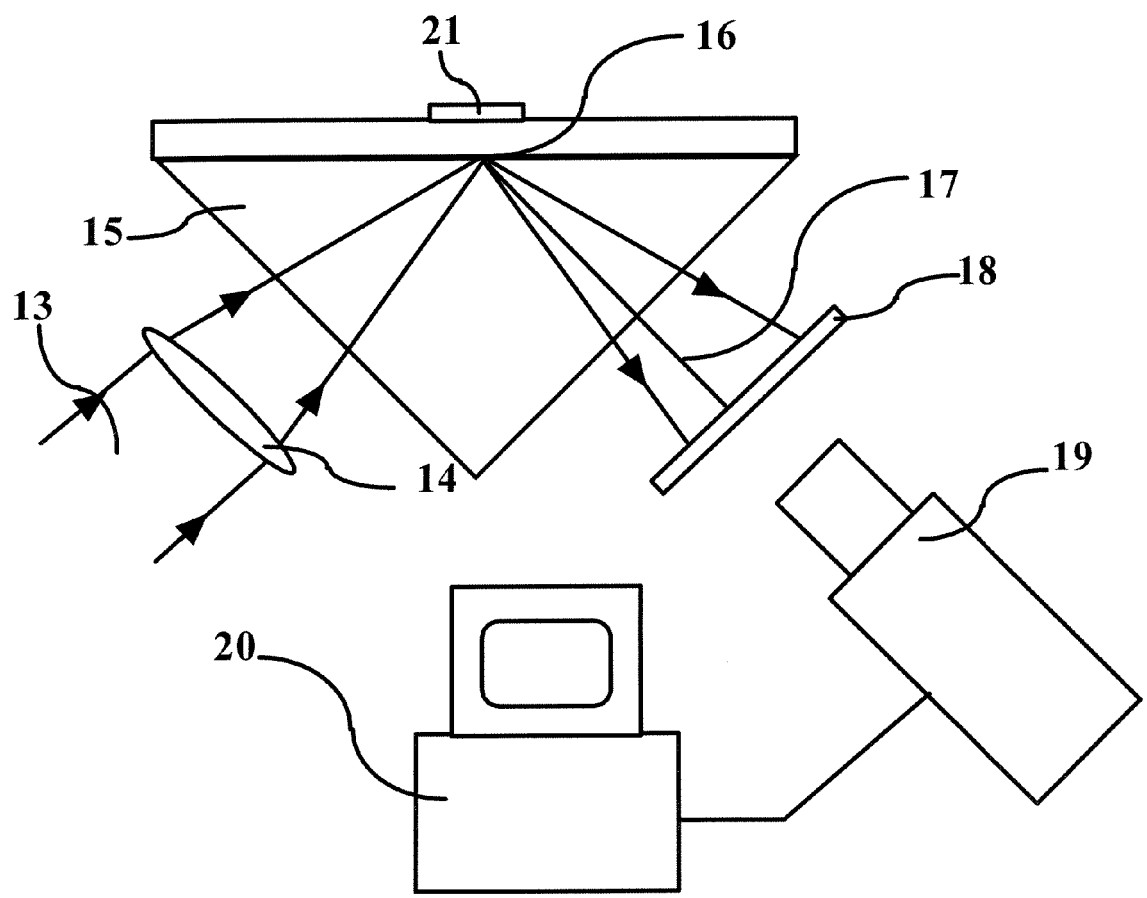
FIG. 5 is a top view of a schematic layout of the elements of another optical coupling arrangement in accordance with another embodiment of the present invention.
Figure 7:
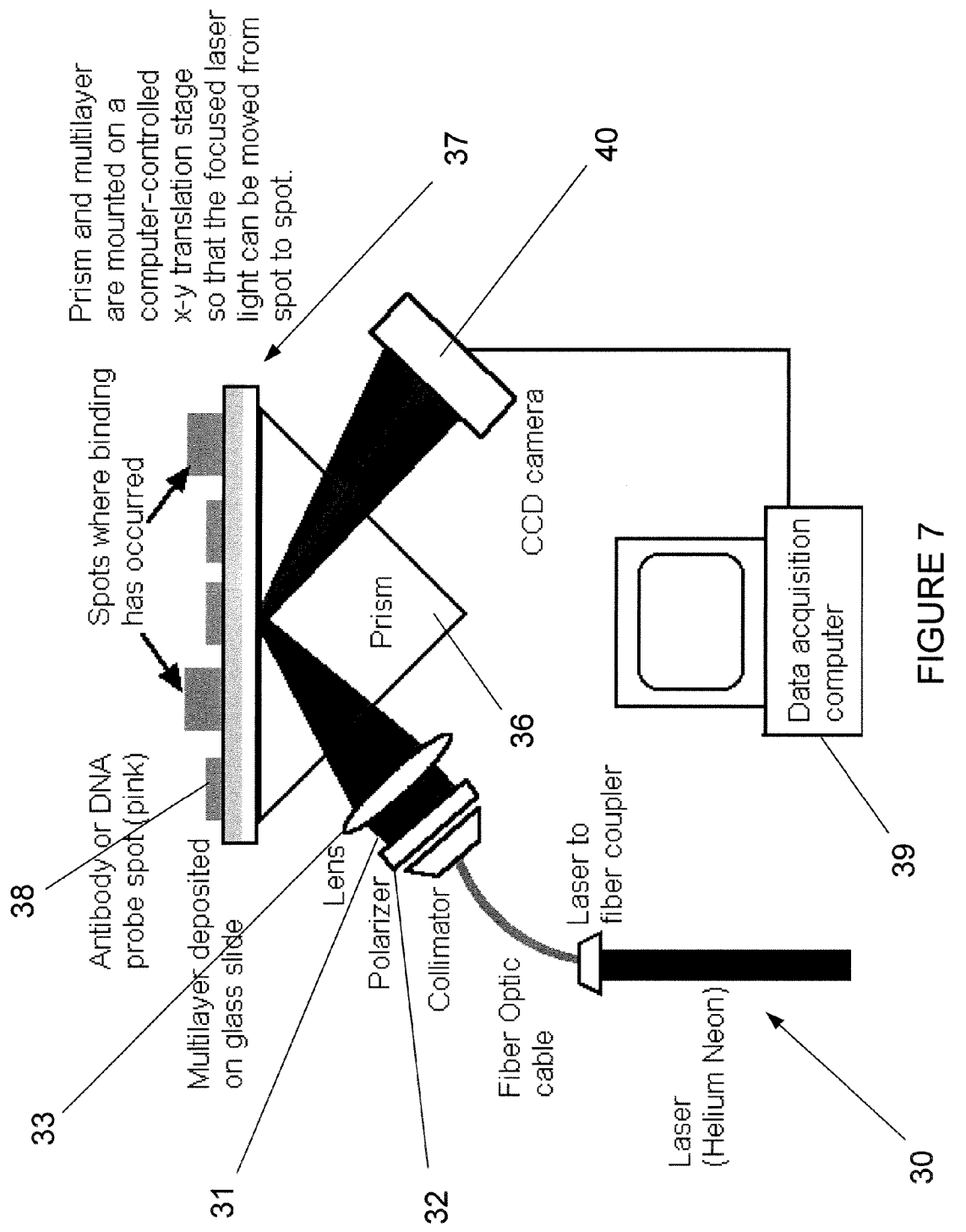
FIG. 7 is a top view of a schematic layout of the elements of another optical coupling arrangement in accordance with another embodiment of the present invention.

FIGS. 2, 5 and 7 show three different sensor configurations that make use of a prism 8, 15 to facilitate the coupling of light to surface electromagnetic waves. The dispersion of surface electromagnetic waves is such that they are non-radiative, which means that they do not couple directly to light. A prism 8, 15 or a grating configuration thus may be used to phase match incident light and facilitate resonant coupling to the surface electromagnetic modes The phase-matching requirements governing optical excitation of surface electromagnetic waves means that each wavelength of light has a specific coupling angle. The sensor configurations shown in FIGS. 2 and 5 keeps one of these parameters (i.e., wavelength or angle) fixed, and monitors the change the other parameter.

FIGS. 2 and 5 show the multilayer 2 as being placed on a substrate 1 as described above, and the substrate 2 being attached to the base or reflecting side of the prism 8, 15, although in some embodiments the multilayer 2 can be directly deposited onto the base or reflecting side of the prism 8, 15.

FIG. 2 shows an exemplary configuration using a broad wavelength light source 5 incident at one fixed angle of incidence through a prism 8. The light source 5 is a broad wavelength source (for example, a light emitting diode or a tungsten lamp filtered by a linear variable filter to provide a band of wavelengths). The light may be emitted through a pinhole or from the end of a fiber optic cable, and then collimated by a lens 6. The parallel light is incident onto the optical multilayer structure 7 through the prism 8. The angle of incidence of the light is above the angle for total internal reflection. In embodiments where the multilayer 2 is not deposited on the prism 8, the transparent substrate 1 of the optical multilayer structure 7 may be attached to the prism by any acceptable means, including, but not limited to, index-matching fluid. The reflected light is directed to a lens 9 that collects and directs the light to an optical spectrometer 10. As shown in FIG. 2, the activated surface of the multilayer structure 7 may be located in a flow cell 11. A flow cell arrangement is useful for many testing arrangements; however, it is not a necessary component for the sensor. In another exemplary embodiment, for example, a fixed wavelength configuration may be used to perform experiments in air.

Figure 3:
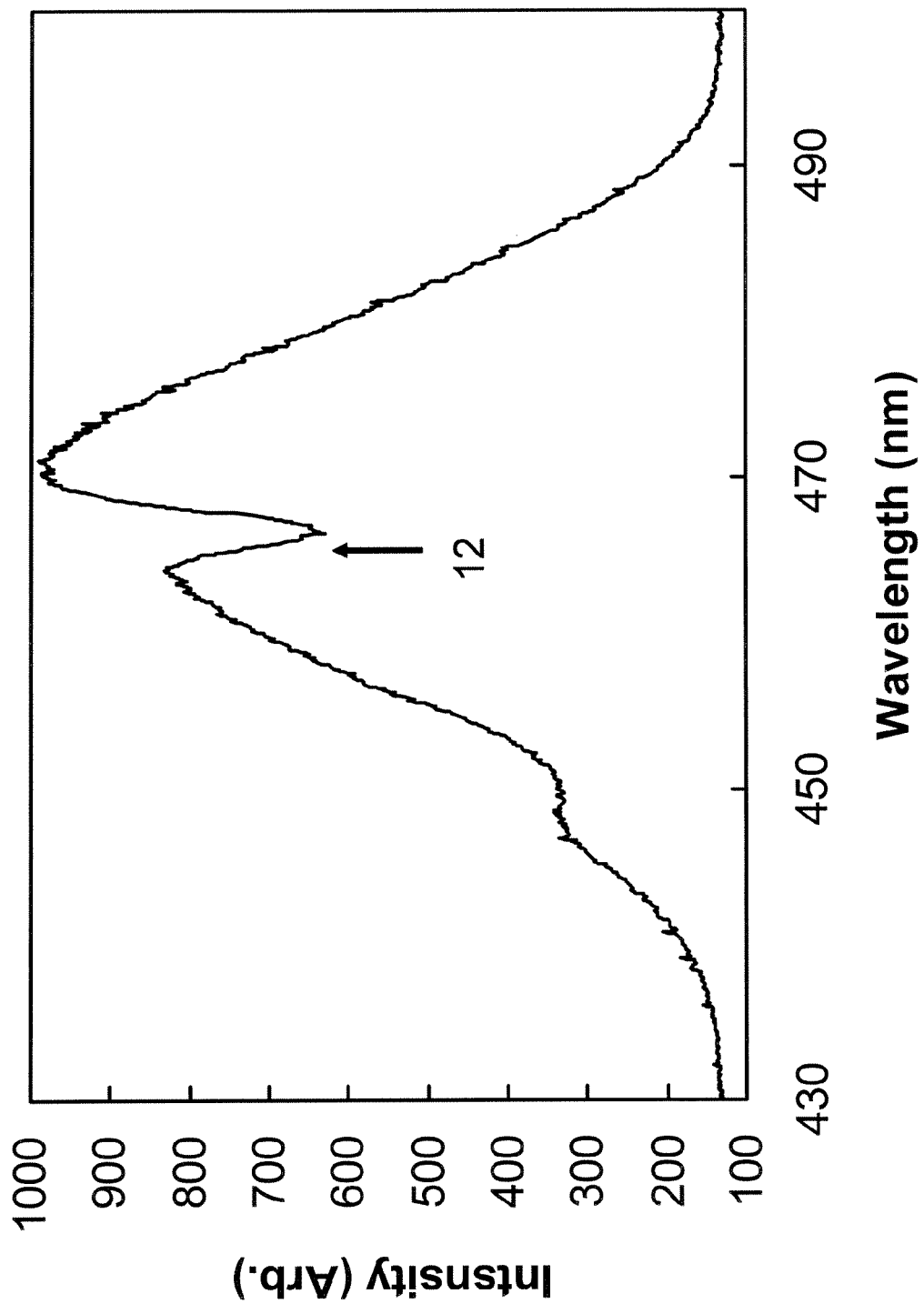
FIG. 3 is a plot of a spectrum demonstrating coupling in accordance with one embodiment of the present invention.

FIG. 3 shows a plot of a spectrum demonstrating coupling to the surface electromagnetic mode in accordance with one exemplary embodiment of the present invention. The broad spectrum shows light intensity from below 450 nm to above 490 nm. Coupling of one narrow band of wavelengths near 465 nm to the surface electromagnetic mode is shown by the drop in intensity 12.

Figure 4:
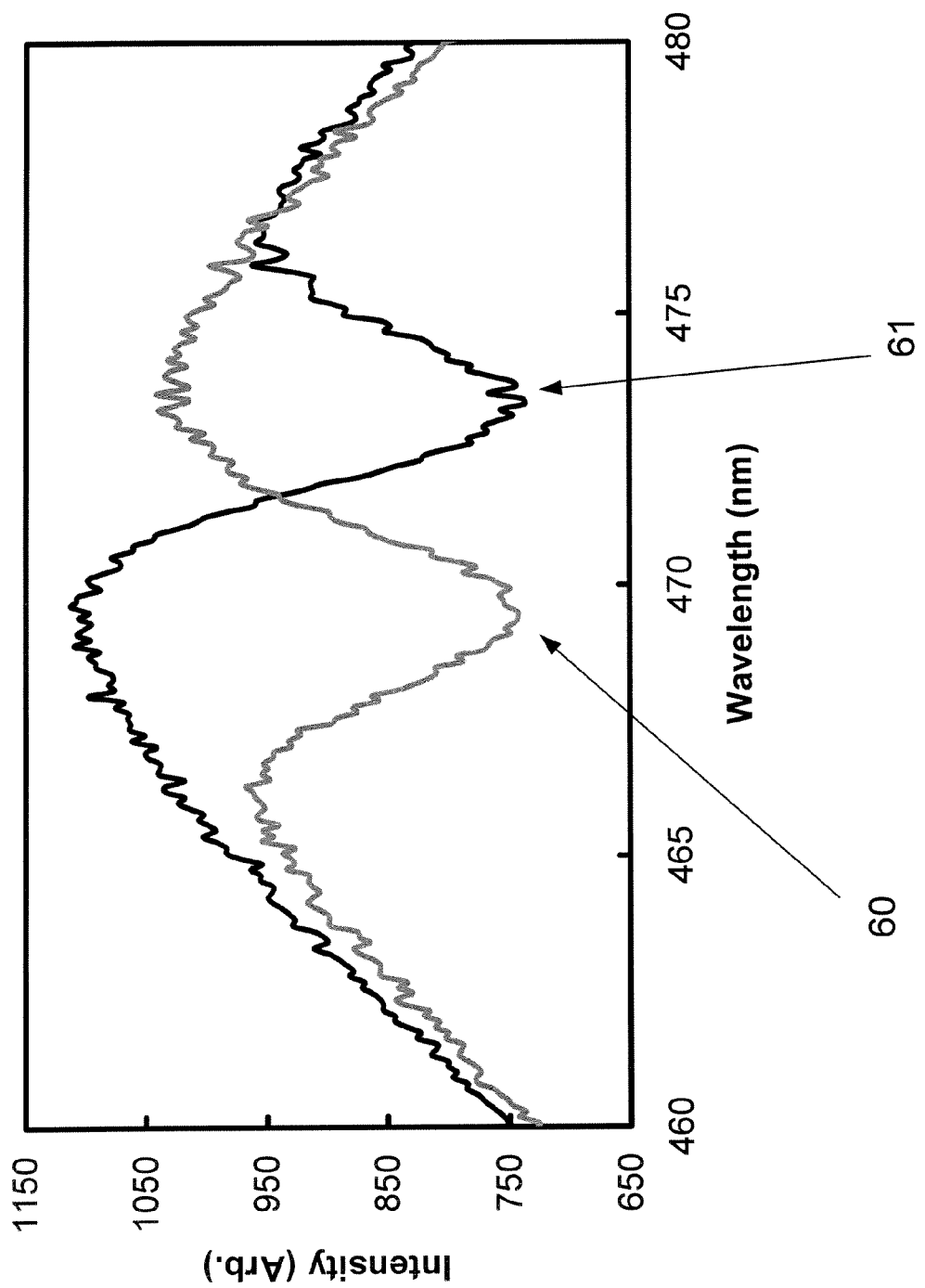
FIG. 4 is a plot of results of one sample test in accordance with one embodiment of the present invention.

FIG. 4 demonstrates an example of how the fixed wavelength configuration arrangement may be used as a sensor. In this example, the optical multilayer structure 7 was prepared with a 20-mer DNA probe designed to bind to a segment of the DNA of a specific influenza virus. The dip on the left 60 (just below 470 nm) is with the flow cell 11 filled with buffer solution before any exposure of the prepared multilayer slide. The dip on the right 61 is after exposure to a solution containing the influenza DNA. After sufficient exposure time, the flow cell 11 was again flushed and filled with buffer to remove any unbound DNA. The shift in the wavelength of coupling to the surface mode results from the change in surface conditions on the multilayer due to binding of the influenza DNA in solution to the probe DNA on the surface (n.b., influenza is a single stranded negative polarity RNA virus). The genome exists as eight separate segments. For this embodiment, the RNA was reverse transcribed and amplified using primers that allow amplification of the entire NS gene, 890 nucleotides. Primer sequences were: forward: 5' AGCAAAAG-CAGGGTGACAAA, reverse: 5' AGTAGAAACAAGGGT-GTTTT. The amplicon was cloned into pGEM-T and transformed into *E. coli* JM109. Template for amplification for sensor analysis was obtained by boiling an overnight broth of *E. coli* transformants and using the primers listed above. Similar results may be obtained for protein testing, including but not limited to antibody-antigen binding.

It should be noted that in flow cell experiments the shift of the surface mode can be followed as a function of time after the beginning of the exposure. This procedure permits the tracking of rate dynamics of binding of the probe and target species.

FIG. 5 shows another exemplary sensor configuration using a single wavelength light source (e.g., a laser) whose light is focused to provide a range of incident angles. The light or radiation source in this exemplary embodiment is a laser with a fixed stable wavelength (for example, a Helium-neon laser). The light may be expanded and collimated. As shown in FIG. 5, the collimated light 13 is passed through a focusing lens 14 and into the prism 15 in order to create a small focal spot on the multilayer structure 16.

Of the range of angles contained in the focused beam, only the monochromatic light at one angle of incidence will couple to the surface electromagnetic modes and thus be attenuated in the reflected light. This missing light is discernable as a narrow dark line 17 in the diverging light that exits the prism 15. The diverging light from the prism is captured by any one of a variety of light capturing devices or means. For example, a screen 18 and a CCD camera 19 may be used, as shown in FIG. 5. Alternatively, the light may be directly captured on a CCD array or other 2-dimensional light sensing arrangement. The captured image may then be fed to a computer 20 and analyzed using an image processing routine to determine the angular position of the minimum in the reflected light intensity. The position of this minimum changes with dielectric loading (e.g., mass or refractive index change) on the surface providing sensing action.

The fixed wavelength arrangement can be used to do flow cell 11 experiments of the type described above. The small focused spot may provide an advantage in these experiments, compared to the fixed angle configuration, because the area of the activated region on the multilayer structure 16 can be made smaller and the volume of the flow cell 11 reduced. These advantages can result in the use of less of the reagents in the experiment, thereby reducing cost.

The fixed wavelength arrangement can also be used to perform scans in a dry arrangement in which arrays of sensitized spots (for example, antibody or DNA probe) are deposited in a regular arrangement using a commercial arrayer. Each spot of the array can be sensitized to detect a specific DNA or protein allowing a sample to be tested for a large number of targets in a single experiment. The spots are exposed to a solution of the sample to be tested and then washed and dried. The slide is then placed in optical contact with the prism using index matching fluid. Using precision motorized control stages typically under computer control, a two-dimensional scan is performed on the array of exposed spots. The surface mode reflectivity dip shifts in its angular position in proportion to the degree of mass loading (for example antibody-antigen binding) that has occurred.

Figure 6:
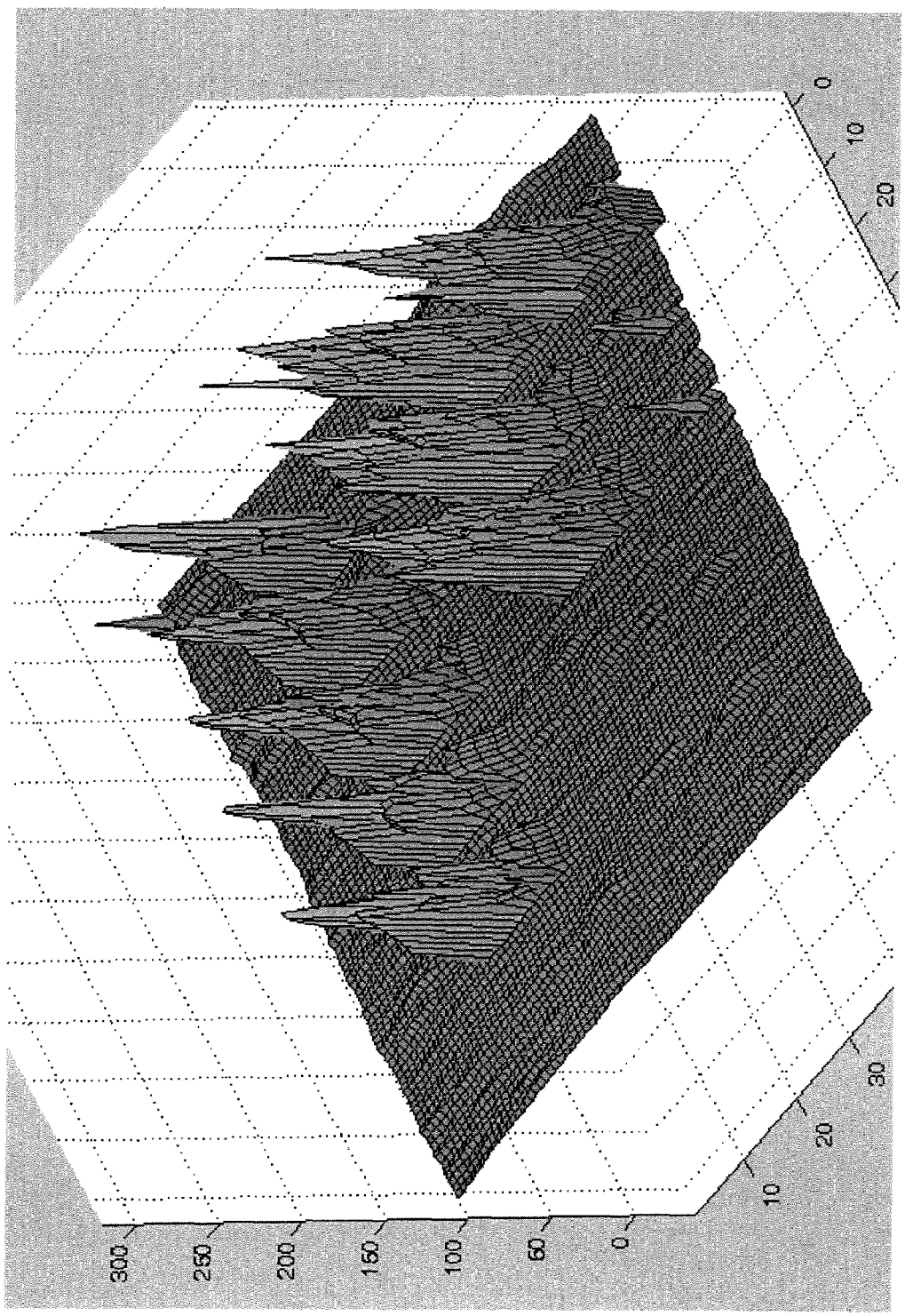
FIG. 6 is a three-dimensional plot of results of one experimental scan in accordance with one embodiment of the present invention.

FIG. 6 shows an experimental scan over a 5×3×1 arrangement of arrayer-deposited spots of protein (500 microns in diameter) illustrating the ability to create a two-dimensional profile of surface features. The protocol of using dry spots is a close parallel with the fluorescence method used currently in monitoring biological reactions. The advantage of the surface electromagnetic wave method is that it does not require the use of fluorescent tags. Furthermore, the sensitivity of the method allows the detection quantities of biomolecular material lower than that typically observable in fluorescence scanning of spot arrays.

FIG. 7 shows an arrangement to realize one exemplary embodiment of a microarray-based assay sensor configuration. In the exemplary embodiment, a one-dimensionally periodic PBG multilayer structure 37 composed of alternating layers of high and low refractive index materials (e.g., $TiO_2$ and $SiO_2$ respectively) are deposited on a glass slide substrate or directly on the base of the prism 36, as described above. Although this simple embodiment does not possess a photonic band gap in all propagation directions, it is an excellent choice for sensing applications because such multilayers can be fabricated accurately and their surface optical wave properties are well understood. In other exemplary embodiments, multi-dimensional periodic PBG material may be used.

To begin a microarray screening assay for a particular target, probe biomolecules 38 are attached to the surface of the PBG multilayer structure 37. A chemical binding layer may be used to ensure that biomolecules placed by the arrayer adhere to the PBG multilayer structure 37 surface. In one exemplary embodiment, the outer layer of the PBG may be $SiO_2$ (i.e., glass) so that immobilization chemistries currently developed for fluorescence detection of microarrays can be used directly. Arrays may be deposited using a microarrayer known in the art, such as, but not limited to, a SpotBot microarrayer Telechem International Inc. The number, size and spacing of the spots may vary. In one exemplary embodiment, the spots are protein spots ranging from 265 microns in diameter spaced by 750 microns, with 35 total spots. The number of spots may be increased in some embodiments to approximately 20,000, or more.

In an exemplary embodiment, the method of using the microarray configuration comprises placement of a probe array, obtaining a reference scan with the surface optical wave array reader, exposure of the array to the target or targets, and performance of a final scan. By comparing the scans before and after exposure to the targets, one can determine where binding has occurred. The coupling prism 36 is movable, and may be mounted to a computer-controlled x-y translation stage. If the multilayer 2 is not deposited directly on the prism 36, the multilayer structure 37 and the microarray to be scanned may be optically attached to the base side or reflecting face of the prism using index-matching fluid. Collimated light 31 from a laser 30 (such as a Helium-Neon laser, as shown) is focused, typically by a focusing lens 33, to a small area through the prism 36 and substrate 1 onto the PBG multilayer 2. The light 31 may be polarized 32. Although the focused beam contains light at a range of angles, all the light is incident at angles greater than that for total-internal reflection so that the majority of the light exits the prism 36 in an expanding cone. A small portion of the light in the focused beam is incident at the correct angle to permit phase matching to the surface optical waves on the PBG surface. Light that resonantly couples to surface optical waves is lost from the reflected beam and its absence is indicated by a narrow dark line in the expanding cone of light. The angular position of the dark line is determined by capturing an image of the expanding beam with a light capturing device. As shown in FIG. 7, the light capturing device may be a CCD camera 40 connected to a frame-grabbing card in the control computer 39.

The computer 39 moves the x-y stage such that the focused optical beam is raster scanned across the area of the PBG multilayer structure 37 that contains the microarray. When the optical beam moves from a bare PBG region onto one of the microarrayed spots the surface optical wave resonance conditions are altered leading to a shift in the angular position of the dark line in the captured CCD image. The magnitude of the angular shift is proportional to the dielectric loading (thickness and refractive index) due to the biomaterial in the microarrayed spot, which means that it is possible, in principle, to obtain size and conformational information about molecular monolayers bound to the surface. A program coordinates the x-y stage movement, grabs and analyzes the image to find the angular position of the dark line, and stores the corresponding data in an array. The final array is representative of the surface topography of the microarray—x and y representing position in the plane of the slide, and z the "height" of the biomolecular spot.

Figure 8:
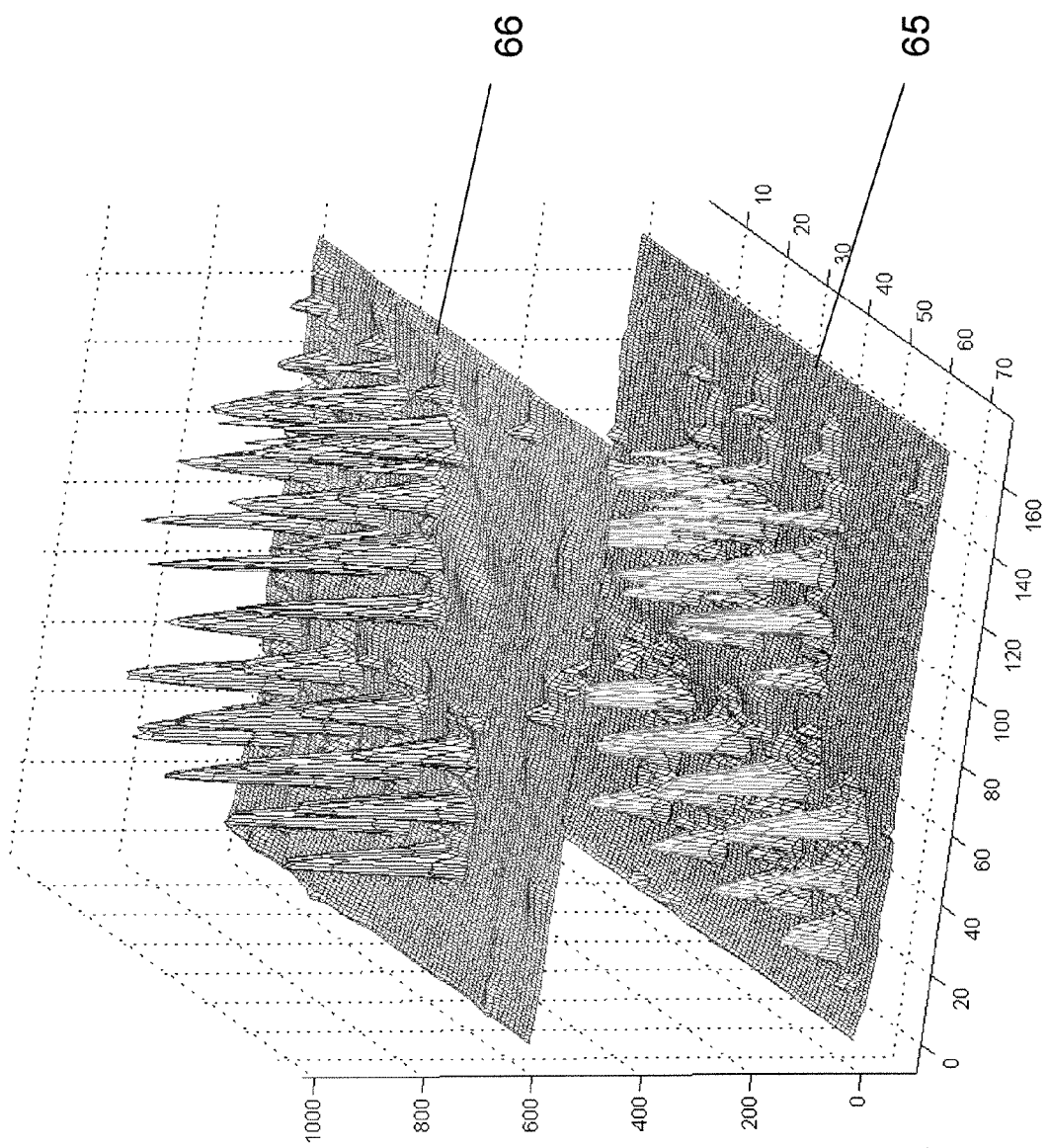
FIG. 8 is a pair of three-dimensional plots of before and after results of experimental scans in accordance with one embodiment of the present invention.
Figure 9:
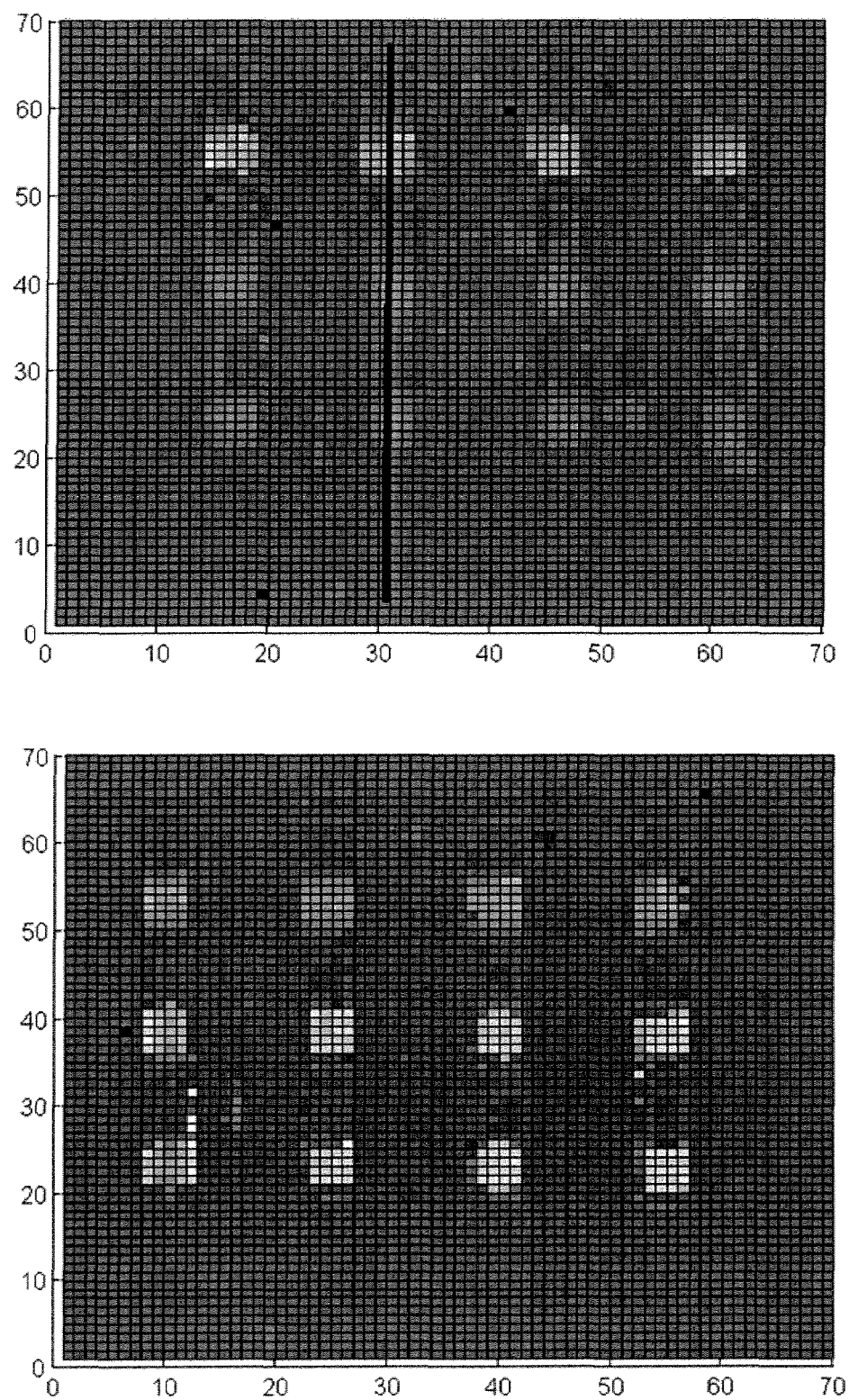
FIG. 9 is a view of sample tests in accordance with one embodiment of the present invention.
Figure 10:
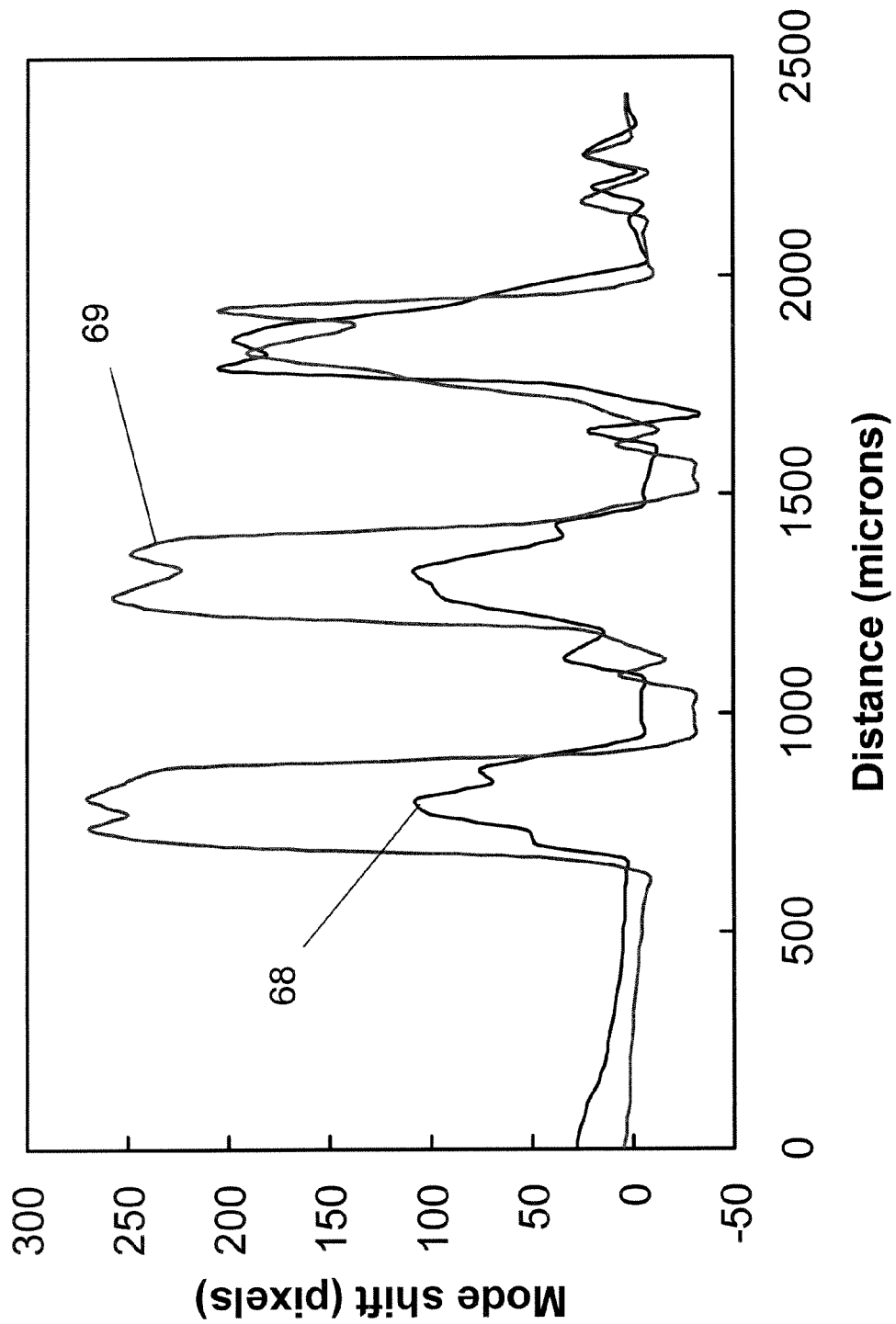
FIG. 10 is a plot of sample test results in accordance with one embodiment of the present invention.

An example of the results of exemplary before and after scans are shown in FIG. 8. The two plots are offset; the reference scan 65 is below the after-exposure scan 66. The rows of spots that recede into the page are all identical replicas so by comparison of the plots it is possible to tell that binding occurs on rows 1, 2, 4, and 7 (reading rows from left to right). To demonstrate a more quantitative determination of the binding, FIG. 9 plots a head-on view of a subset of the original array (rows 1-3 from FIG. 8). The top row of spots remains unchanged in intensity from one scan to the next whereas the lower two rows clearly increase. This difference is quantified by the plot in FIG. 10 that shows a line scan through the second column of spots for both the reference 69 (red) and after-exposure scans 68 (blue).

The experimental results shown FIG. 9 are an example of a blind run test of an exemplary embodiment of the present invention. FIG. 9 shows rows (going from top to bottom) consisting of Sheep IgG, Bovine Serum Albumin (BSA) with Cy5 label, and BSA with no label. After the reference scan (top) was performed, the slide was exposed to sheep anti-BSA (with a FITC label) and binding to both rows of the BSA but not to Sheep IgG was observed. The upper image is the reference scan and the lower image is the scan after binding. It should be noted that only after the experiment was completed, and binding/non-binding assignments made for each spot, were slides examined to compare sensor results. The analysis of microarrays based on surface optical wave resonance in photonic band gap materials and its use in detecting protein binding reactions offers a number of advantages over existing microarray readout technologies. First, the method is label-free—it does not require the use of fluorescent or radio-active tags to detect binding. Second, the surface optical wave method has the potential for high throughput and ease of use. Spot arrays may be deposited using a commercial microarrayer and scans may be performed on as-prepared slides without the use of flow-cells or micro-fluidic arrangements. Third, the technique has high sensitivity. Surface optical waves in PBG materials are analogous to surface plasmons in metal films. Both are non-radiative electromagnetic modes that can be resonantly generated through prism or grating mediated optical coupling. Similarly both excitations can be configured to exhibit sensing action that derives from a shift in resonance conditions due to binding of a target entity. However, dielectric loss in PBG materials is orders of magnitude less than in metals that support surface plasmons. Low loss translates to narrow resonance widths and, hence, to concomitantly high sensitivity. Finally, one-dimensional PBG can be accurately manufactured using existing thin-film fabrication methods. They can be designed to work in any desired wavelength range, they are mechanically and chemically robust, and, by appropriate choice of final layer material, they offer flexibility in immobilization chemistry.

Accordingly, the present invention discloses several variations of a new, highly sensitive chemical, optical, and biochemical sensing method and apparatus using PBG multilayers. The extremely low loss and the ability to engineer the optical properties of the active material make the potential capabilities and applications much richer than known surface plasmon sensors and similar devices. With the present invention, surface EM wave resonances are very sharp, which translate to extremely high sensitivity to dielectric loading at the surface. In addition, PBG multilayers can be designed to be surface active at essentially any wavelength, including wavelengths in the blue and ultraviolet ranges where surface plasmon sensors are not viable. Operation at shorter wavelengths can further enhance sensitivity to thin overlayers. Furthermore, the confinement of the surface EM mode to the surface can be engineered in order to optimize the sensor for a thickness range of dielectric overlayer.

Another advantage is that PBG multilayers can be made from a variety of combinations of high and low index materials. Many of these materials are mechanically and chemically robust, allowing the development of sensors suitable for hostile environments. For example, PBG multilayers made from alternating layers of $TiO_2$ and $SiO_2$ deposited on glass slides are sufficiently robust to permit multiple cleaning and reuse of slides. In addition, PBG multilayers are amenable to accurate, high-volume manufacturing using existing commercial thin film deposition technology.

Thus, it should be understood that the embodiments and examples have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art. Accordingly, it is intended that the scope of the invention be defined by the claims appended hereto.

I claim:

1. An optical multilayer structure, comprising:
    a substrate;
    an optical multilayer deposited on the substrate, said optical multilayer comprising a series of alternating layers of high refractive index materials and low refractive index materials, wherein the high refractive index materials and low refractive index materials are not metals, and further wherein the thickness of the layers is selected so as to cause the structure to exhibit a photonic band gap; and
    a terminating layer deposited on the optical multilayer opposite the substrate, wherein the terminating layer is selected such that a surface optical mode exists at a wavelength within the photonic band gap, and further wherein the terminating layer comprises a material other than a material used for the series of alternating layers.

2. The optical multilayer structure of claim 1, wherein there is at least one layer of a high refractive index material and at least one layer of a low refractive index material.

3. The optical multilayer structure of claim 1, wherein said optical multilayer comprises a series of alternating layers of a single high refractive index material and a single low refractive index material.

4. The optical multilayer structure of claim 1, wherein the terminating layer is glass.

5. The optical multilayer structure of claim 1, wherein there is resonant coupling between the surface optical mode and incident light on the optical multilayer structure.

6. The optical multilayer structure of claim 5, wherein the resonant coupling varies upon exposure of the optical multilayer structure to a material or substance to be tested.

7. The optical multilayer structure of claim 1, further comprising a sensing layer deposited on the terminating layer opposite the optical multilayer.

* * * * *